US012230109B2

(12) United States Patent
Denny et al.

(10) Patent No.: US 12,230,109 B2
(45) Date of Patent: Feb. 18, 2025

(54) MEDIA SANITIZING CASSETTE AND METHOD OF OPERATION

(71) Applicant: NCR Atleos Corporation, Atlanta, GA (US)

(72) Inventors: Ian McFarlane Denny, Perth (GB); Stephen Anderson, Perthshire (GB); Grant A. McNicoll, Carnoustie (GB); Graeme Smith, Dundee (GB)

(73) Assignee: NCR Atleos Corporation, Atlanta, GA (US)

( * ) Notice: Subject to any disclaimer, the term of this patent is extended or adjusted under 35 U.S.C. 154(b) by 0 days.

(21) Appl. No.: 18/397,260

(22) Filed: Dec. 27, 2023

(65) Prior Publication Data

US 2024/0135786 A1    Apr. 25, 2024

Related U.S. Application Data

(63) Continuation of application No. 18/121,914, filed on Mar. 15, 2023, now Pat. No. 11,983,999, which is a (Continued)

(51) Int. Cl.
*G07F 19/00* (2006.01)
*A61L 2/10* (2006.01)
*G07G 1/00* (2006.01)

(52) U.S. Cl.
CPC ............. *G07F 19/205* (2013.01); *A61L 2/10* (2013.01); *G07F 19/201* (2013.01); *A61L 2202/10* (2013.01); *G07G 1/0027* (2013.01)

(58) Field of Classification Search
CPC .......... G07F 19/205; G07F 19/201; A61L 2/10
(Continued)

(56) References Cited

U.S. PATENT DOCUMENTS 9,117,327 B1 * 8/2015 Wasil ................. G06Q 20/1085
11,354,984 B2   6/2022 Denny et al.
(Continued)

OTHER PUBLICATIONS

U.S. Appl. No. 16/881,856 U.S. Pat. No. 11,354,984, filed May 22, 2020, Media Sanitizing Cassette and Method of Operation.
(Continued)

*Primary Examiner* — Daniel A Hess
(74) *Attorney, Agent, or Firm* — Schwegman Lundberg & Woessner, P.A.

(57) ABSTRACT

A valuable media sanitizing/cleansing cassette is provided for sanitizing/cleansing surfaces of valuable media dispensed to a consumer during a dispense transaction at a transaction terminal. Dispensed media is urged from one or more media cassettes within the terminal along a transport path. The transport path is altered to pass the media through the sanitizing/cleansing cassette where the top and bottom surfaces of the media are illuminated with Ultraviolet (UV) radiation to eradicate any bacteria or virus that may be adhered to the top or the bottom surfaces of the media. Once the media passes through the sanitizing/cleansing cassette, the now sanitized/cleansed media is urged along a remainder of the transport path and dispensed from a media interface of the terminal to the consumer. In an embodiment, media deposited at the terminal is also sanitized/cleansed by passing through the sanitizing/cleansing cassette before being stored in the appropriate media cassettes.

18 Claims, 15 Drawing Sheets

Related U.S. Application Data continuation of application No. 17/690,324, filed on Mar. 9, 2022, now Pat. No. 11,676,459, which is a continuation of application No. 16/881,856, filed on May 22, 2020, now Pat. No. 11,354,984.

(58) Field of Classification Search
USPC .......................................................... 235/379
See application file for complete search history.

(56) References Cited

U.S. PATENT DOCUMENTS

| | | |
|---|---|---|
| 11,676,459 B2 | 6/2023 | Denny et al. |
| 2011/0253563 A1 | 10/2011 | Goldman |
| 2011/0308917 A1 | 12/2011 | Lathem |
| 2012/0211645 A1 | 8/2012 | Tullo et al. |
| 2013/0045133 A1 | 2/2013 | Maguire |
| 2015/0306263 A1 | 10/2015 | Yanke |
| 2017/0035923 A1 | 2/2017 | Yanke |
| 2020/0306395 A1 | 10/2020 | Gardiner et al. |
| 2021/0308296 A1 | 10/2021 | Cook et al. |
| 2021/0330832 A1 | 10/2021 | Dobbins et al. |
| 2021/0330835 A1 | 10/2021 | Hunt |
| 2021/0346538 A1 | 11/2021 | Haddon |
| 2022/0198885 A1 | 6/2022 | Denny et al. |

OTHER PUBLICATIONS

U.S. Appl. No. 17/690,324 U.S. Pat. No. 11,676,459, filed Mar. 9, 2022, Media Sanitizing Cassette and Method of Operation.

U.S. Appl. No. 18/121,914, filed Mar. 15, 2023, Media Sanitizing Cassette and Method of Operation.

"U.S. Appl. No. 16/881,856, Notice of Allowance mailed Feb. 14, 2022", 10 pgs.

"U.S. Appl. No. 17/690,324, 312 Amendment filed Apr. 26, 2023", 6 pgs.

"U.S. Appl. No. 17/690,324, Non Final Office Action mailed Oct. 14, 2022", 8 pgs.

"U.S. Appl. No. 17/690,324, Notice of Allowance mailed Feb. 1, 2023", 9 pgs.

"U.S. Appl. No. 17/690,324, Preliminary Amendment filed Mar. 23, 2022", 6 pgs.

"U.S. Appl. No. 17/690,324, Response filed Jan. 17, 2023 to Non Final Office Action mailed Oct. 14, 2022", 8 pgs.

"U.S. Appl. No. 18/121,914, Non Final Office Action mailed Jun. 29, 2023", 9 pgs.

"U.S. Appl. No. 18/121,914, Notice of Allowance mailed Oct. 16, 2023", 9 pgs.

"U.S. Appl. No. 18/121,914, Preliminary Amendment filed Apr. 11, 2023", 6 pgs.

"U.S. Appl. No. 18/121,914, Response filed Oct. 2, 2023 to Non Final Office Action mailed Jun. 29, 2023", 7 pgs.

\* cited by examiner

MEDIA SANITIZING CASSETTE AND METHOD OF OPERATION

CROSS-REFERENCE TO RELATED APPLICATION

This application is a continuation of U.S. patent application Ser. No. 18/121,914, filed Mar. 15, 2023, which is a continuation of U.S. patent application Ser. No. 17/690,324, filed Mar. 9, 2022, which is a continuation of U.S. patent application Ser. No. 16/881,856, filed May 22, 2020, which applications and publications are incorporated herein by reference in their entirety.

BACKGROUND

As a result of the current COVID-19 pandemic, consumers/businesses are rightly concerned with handling cash and operating self-service cash-accepting and dispensing devices, such as Automated Teller Machines (ATMs) or Self-Service Terminals (SSTs). Currency is made of paper-based and/or polymer-based materials where pathogens such as bacteria and viruses are known to be capable of lingering on the surfaces. In short, handling cash has never been a sanitary exercise but during the pandemic handling cash can be life threatening, especially to those individuals that are at high risk for contracting or developing complications of disease.

During the pandemic, some business have stopped accepting currency as a form of payment for their goods and services. These businesses may require alternatives such as payment cards for their goods and services. The problem with this is that a large portion of the population lacks any payment cards for a variety of reasons, such as an inability to obtain due to credit problems, an already exhausted credit limit, concerns about privacy and anonymity, or may be unbanked for other reasons. Consequently, businesses that stop accepting currency have essentially closed off access to their goods and services for a large segment of the population.

Additionally, some businesses are cash-only businesses and require access to ATMs during non-banking hours to deposit cash proceeds for security or regulatory. For example, because of a lack of harmonization among some or the United States and federal government some businesses may not be able reliably to accept card payments. Some businesses may rely on ATMs to make cash deposits during the pandemic.

Furthermore, consumers need access to cash during the pandemic to pay for essential services, such as food, utilities, gas, housing, etc. As a result, during the initial weeks of a pandemic many financial institutions may experience unusual high demand for cash withdrawals at their ATMs.

Cash is vital to the proper function of the economy and banks are the primary distribution point where consumers can obtain and deposit their cash. Yet, cash is made of paper-based and/or polymer-based material and recognized as a medium through which pathogens may be transmitted from person to person.

Therefore, there is a need for financial institutions to sanitize and clean currency of any harmful bacteria and virus, and other pathogens so as to slow the spread of transmission and make usage of currency safe and reliable.

SUMMARY

In various embodiments, a valuable media sanitizing/cleansing cassette and method of operation are presented.

According to an aspect, a valuable media sanitizing/cleansing cassette that sanitizes/cleanses valuable media during a valuable media dispense/intake operation from a transaction terminal is presented. The valuable media sanitizing/cleansing cassette include a bacteria and virus sanitizing system and transport gears and/or other mechanisms. The transport gears receive a media item from a transport path within a media dispenser or a recycler of a transaction terminal. The media cassette is configured to: 1) pick the media item off the transport path during a dispense operation via the transport gears; 2) urge the media item a length of the media cassette and back to the transport path; 3) activate the sanitizing system to clean a top and a bottom of the media item and to sanitizes the media item before the media item is placed back on the transport path via the transport gears and ejected through an interface of the dispenser or the recycler to complete the dispense operation at the transaction terminal.

DETAILED DESCRIPTION

Figure 1A:
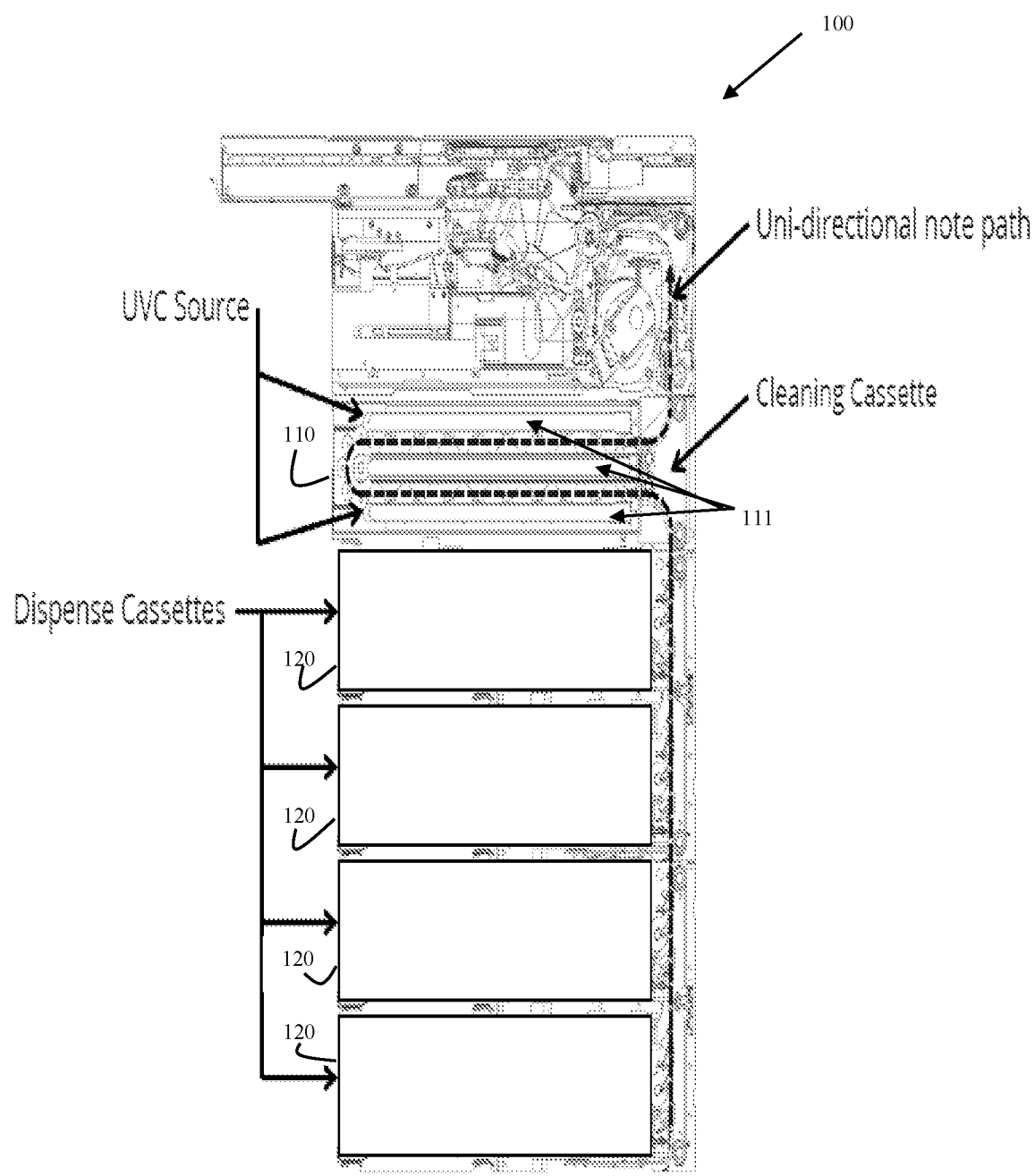
FIG. 1A is a diagram of a media dispenser having a cleaning cassette with a unidirectional note path, according to an example embodiment.

FIG. 1A is a diagram of a media dispenser/recycler having a cleaning cassette with a unidirectional note path, according to an example embodiment. It is to be noted that the components are shown schematically in greatly simplified form, with only those components relevant to understanding of the embodiments being illustrated.

Furthermore, the various components (that are identified in the FIG. 1) are illustrated and the arrangement of the components is presented for purposes of illustration only. It is to be noted that other arrangements with more or less components are possible without departing from the teachings of valuable media sanitization/sterilization during media withdrawals and/or media deposits at a transaction terminal.

As used herein the term "valuable media" refers to currency, bank notes, checks, or any media of value. The terms "valuable media," "media," "banknote," "note," and "currency" may be used interchangeably and synonymously.

A "valuable media depository" refers to a component module of a transaction terminal responsible for storing valuable media for deposit transactions within one or more cassettes of the terminal and responsible for dispensing valuable media from the one or more cassettes during transactions at the transaction terminal.

A valuable media depository can include a media dispenser where deposited media is stored separately from media that is dispensed or the valuable media depository can include a recycler that dispenses media from a same storage where the media is deposited, such that the deposited media is recycled and utilized to fulfill dispense transactions.

A "transaction terminal" refers to a multi-component/module composite device that permits valuable media to be deposited during deposit transactions and withdrawn during dispense transactions. A transaction terminal can include an Automated Teller Machine (ATM), a teller machine (operated by a teller on behalf of customers), a Self-Service Terminal (SST) operated by a customer during a checkout operation at a retail store, or a Point-Of-Sale (POS) terminal operated by a cashier on behalf of a customer during a checkout operation (the POS terminal including a dispenser/recycler and/or safe).

The transaction terminal comprises a variety of components, which are not relevant to the discussions herein other than the depository component that comprises a dispenser and/or recycler. The media when deposited is stored in cassettes within a safe when the same cassettes used for deposited media is used to dispense media for dispense transactions, the component includes a recycler, and when the cassettes used for dispensing transactions is different from other cassettes that house deposit transactions, the component is a dispenser.

A "component" or a "module" may be used synonymously and interchangeably herein and refers to an electromechanical device comprising mechanical parts and electromechanical parts. Electronic circuitry of the module may connect to a processor that is specific to and housed within the module or the electronic circuitry may connect to a processor that is external to and separate from the module.

As used herein a "dispenser" may be referred to as a "dispense module" and a recycler may be referred to as a "recycler module."

As used herein a "pathogen" refers to any bacteria and/or virus that is capable of adhering to or contaminating a valuable media item.

As used herein a "transport path" refers to tracks and/or rollers within a dispenser or recycler and/or a transaction terminal for transporting or urging the media item through the dispenser or the recycler and/or for transporting or urging the media item through other components of the transaction terminal during deposit operations and dispense operations being performed on the transaction terminal.

A "transport path extension" is a pick interface associated with a media cleansing cassette designed to pick a media item off the transport path of the dispenser or the recycler and designed to place the media item back on the transport path once the media item is sanitized within the media cleansing cassette.

A "transport velocity" refers to the travel rate of a media item on the transport path or the travel rate of the media item within the media cleansing cassette.

The transport paths for media being urged through a recycler module can be unidirectional (indicating that media passes through the sanitizing/cleansing cassette once, for example during a dispense operation) or can be bidirectional (indicating that media passes through the sanitizing/cleansing cassette twice (such as once for a deposit of the media and once for a dispense of the media)). Accordingly, a dispenser module may be unidirectional, where the dispenser module does not use the same cassettes for deposits that are used for dispenses.

In an embodiment, two novel sanitizing/cleansing cassettes may be employed for a depository module and a dispenser module, such that the media is cleansed by a first sanitizing/cleansing cassette before being stored in media storage cassettes and other media that are housed in dispense cassettes can pass through a second sanitizing/cleansing cassette during dispense operations. In this way, even transaction terminals that rely on dispense modules can also sanitize deposited media that are deposited in storage media cassettes.

FIG. 1A is a diagram of a media dispenser 100 having a cleaning cassette 110 with a unidirectional note path, according to an example embodiment. The dotted line representing the transport path for dispensed media being dispensed from media cassettes 120. In an embodiment, each media cassette 120 may be associated with a different currency denomination, such as combinations of $1, $5, $10, $20, $50, $100.

During a dispense transaction at the transaction terminal, the dispenser module 100 is instructed to dispense an amount of currency from the cassettes 120. Each currency note is picked from the corresponding currency cassette 120 and pulled from a stack of notes onto the transport path.

Conventionally, such currency notes being dispensed would move vertically up through the dispenser module 100 in a line and urged through a dispenser module interface to a stacking module where the notes are stacked in a bunch and ejected out a pocket outfeed for a customer to take.

This conventional transport path movement is altered by the teaching herein, such that upon reaching a last vertically stacked currency cassette 120 before exiting through the dispenser interface, each currency note is shown urged horizontally along a modified transport path through a novel sanitizing/cleansing cassette 110. The top and bottom surfaces of each currency noted is irradiated by a sanitizing system 111 (such as UV tubes 111) twice (once traveling horizontally for a length of the cassette 110 in a first direction away from the original transport path in the vertical direction where the note is then rotated by the transport path for a second length of the cassette 110 in a second horizontal direction back towards the original transport path in the vertical direction). The note while being urged along the modified transport path through the cassette 110 makes four changes in direction: 1) a first turn from a vertical direction to a horizontal direction to enter the cassette 110 exposing a top of the note to a first UV tube 111 situated above the note and exposing a bottom of the note to a second UV tube 111 situated below the note; 2) a second turn that rotates the note at the end of cassette 110 vertically; 3) a third turn that rotates the note back horizontally, such that the original top of the note is still oriented facing the first UV tube 111 and the bottom of the note is now oriented facing a third UV tube 111; and 4) a fourth turn that changes the horizontal orientation of the note along the transport path back to the original vertical orientation to eject the now sanitized note out through the dispenser module interface for subsequent stacking and ejection from a pocket outfeed of the transaction terminal.

It is noted that for the discussion that follows the sanitizing system 111 is referred to as UV tubes, but as noted below this does not always have to be the case. So, the sanitizing system 111 is referred to as UV tubes 111 for purposes of illustrating one embodiment presented herein and for purposes of comprehension.

Figure 1B:
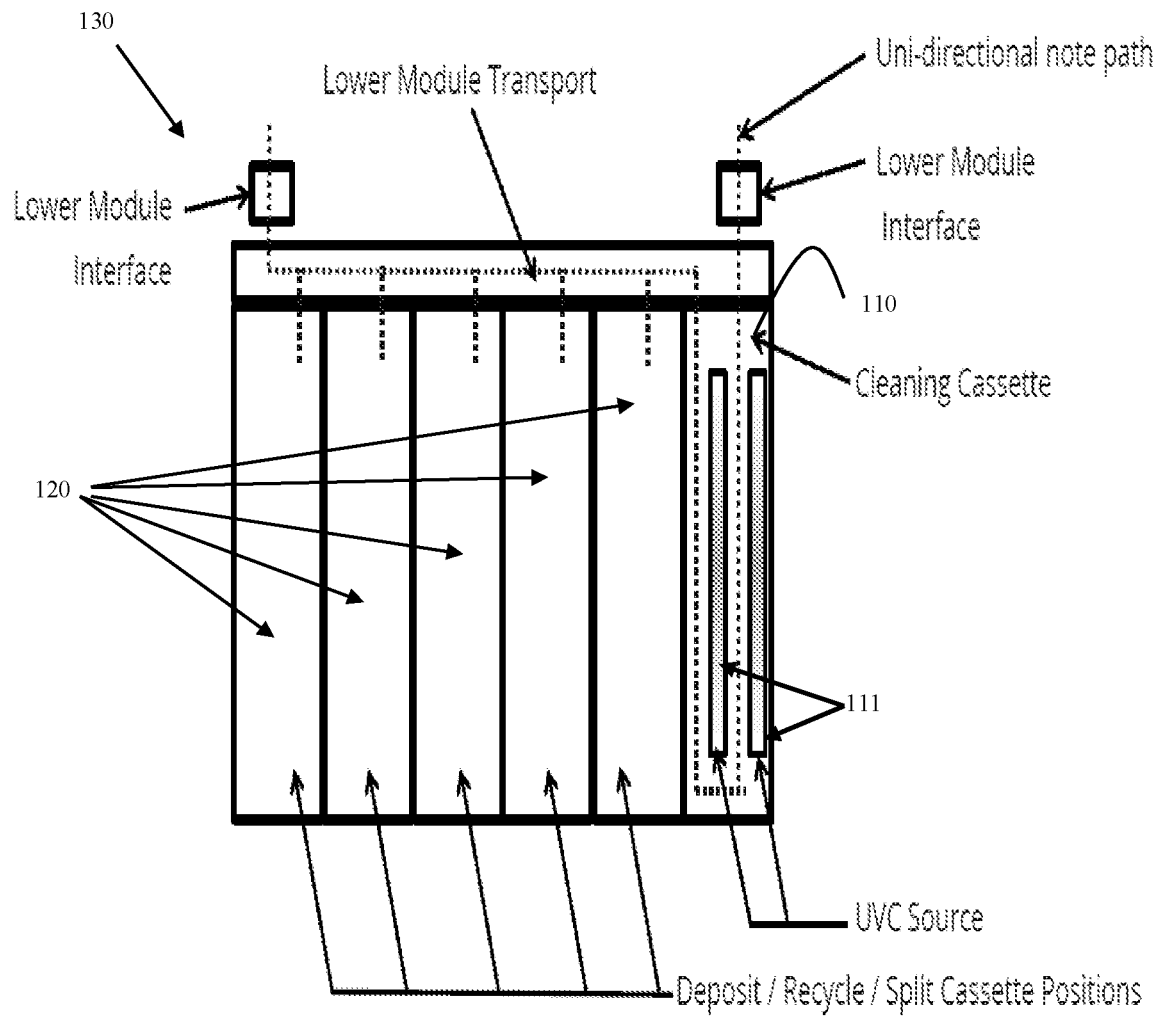
FIG. 1B is a diagram of a recycler having a cleaning cassette with a unidirectional note path, according to an example embodiment.

FIG. 1B is a diagram of a recycler 130 having a cleaning cassette 110 with a unidirectional note path, according to an example embodiment. On deposit of a note, the noted is shown urged down vertically through a first lower module interface and turned horizontally along the transport path where the note is vertically deposited into the appropriate cassette 120 for storage. When the note is subsequently dispensed from the cassette 120, the note is urged vertically off a stack of notes onto the transport path and turned horizontally where it is horizontally urged towards the lower module interface. The note is then urged to turn or change direction three times before being vertically ejected through the lower module interface associated with dispensing the note onto the transport path for subsequent stacking with other notes (when necessary or when the dispense transaction entails more than a single note) and ejected out a pocket outfeed of the transaction terminal. The note is turned a first time from a horizontal orientation to a vertical downward orientation as it is urged through the cassette 110 (the top of the note irradiated by a first UV tube 111). The note is turned a second time from the downward vertical orientation to a horizontal orientation around the first UV tube 111 and then the note is turned a third time in an upward vertical direction such that the top of the note is still exposed to the first UV tube 111 while the bottom of the note is simultaneously exposed to the second UV tube 111.

Figure 1C:
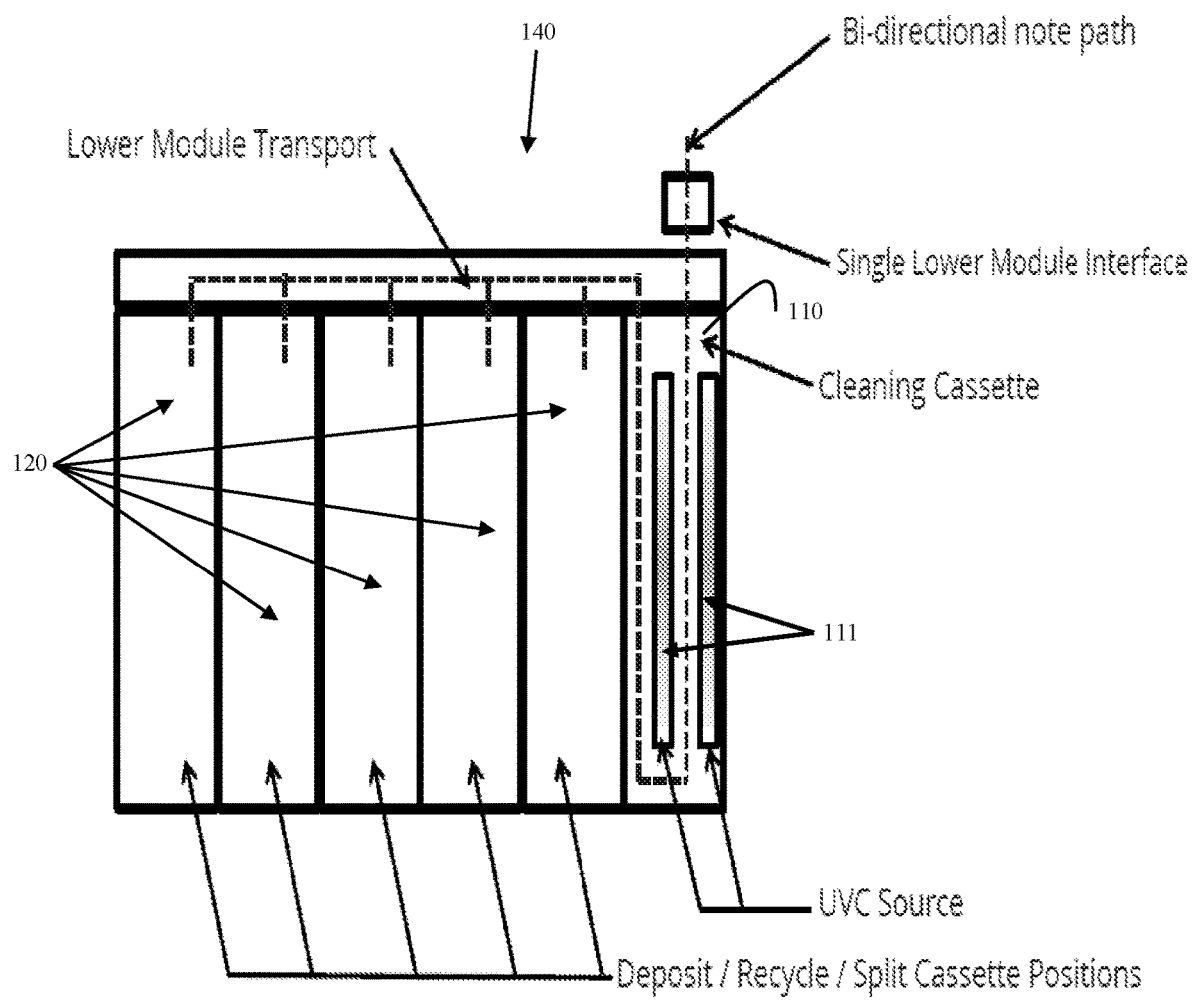
FIG. 1C is a diagram of a recycler having a cleaning cassette with a bidirectional note path, according to an example embodiment.

FIG. 1C is a diagram of a recycler 140 having a cleaning cassette with a bidirectional note path, according to an example embodiment. Both deposited notes and dispensed notes are processed through a same and a single lower module interface. Moreover, both deposited notes and dispensed notes are irradiated by UV tubes 111 when a note is deposited and when the same note is subsequently dispensed. A deposited note changes direction or is turned 4 times 1) urged from a vertical between at least two UV tubes 111 to horizontal; 2) urged from horizontal to vertical around one UV tube 111; 3) urged from vertical to horizontal; and 4) urged from horizontal to vertical to be stacked in the appropriate cassette 120. A dispensed note changes direction or is turned 5 times: 1) picked and urged vertically out of the appropriate cassette 120; 2) urged horizontally towards cassette 110; 3) urged vertically downward with a top of the note facing a first UV tube 111; 4) urged from vertical downward to horizontal around first UV tube 111; and 5) urged from horizontal vertically upward between the first UV tube 111 and second UV tube 111 with the top of the note exposed again to the first UV tube 111 and the bottom of the note exposed to the second UV tube 111; the note is then urged along the transport path out of the single lower module interface to a stacking and pocket outfeed module of the transaction terminal for ejection to the consumer.

It is to be noted that a recycler 130 or 140 may also have horizontally arranged valuable media cassettes 120 and a horizontally arranged media cleansing cassette 110, such as was depicted with dispenser 100. So, the orientation (vertical or horizontal) of the media cleansing cassette 110 and the valuable media cassettes 120 can be different from what is described with FIGS. 1B and 1C.

It is also noted that recyclers 130 or 140 can also include other interfaces besides a pocket or pocket outfeed. Such that specific interfaces presented herein for the recyclers 130 or 140 are intended to be illustrative and are not intended to limit the teachings to a particular type of recycler interface.

Figure 1D:
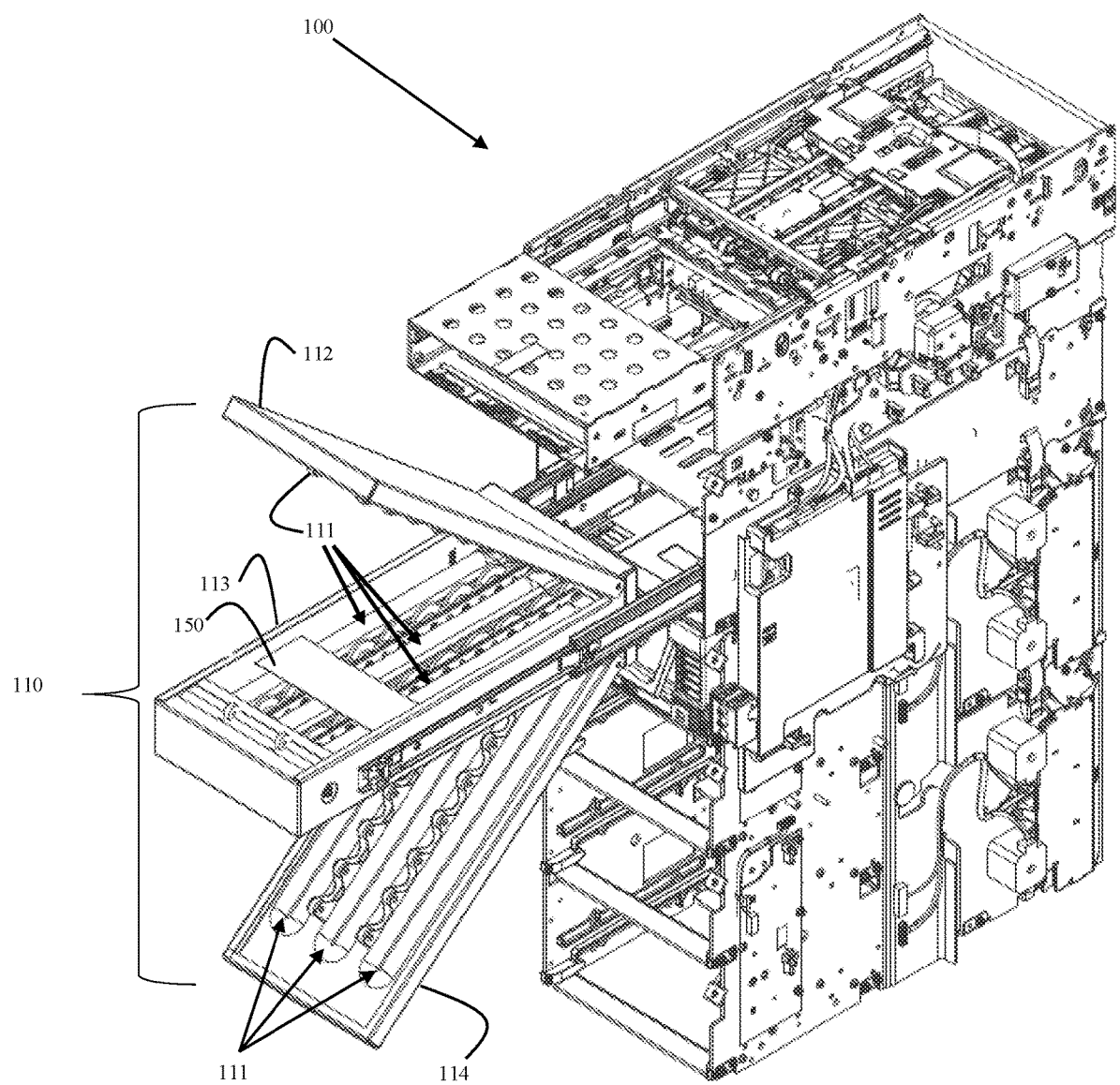
FIG. 1D is a diagram of a partially removed and opened cleaning cassette, according to an example embodiment.

FIG. 1D is a diagram of a partially removed and opened cleaning cassette 110, according to an example embodiment. The cassette 110 includes a top section 112, a middle section 113, and a bottom section 114. Each second 112-114 includes UV tubes 111. Each section 112-114 includes 1 to 3 UV tubes 111 (because of the orientation of FIG. 1D the UV tubes 111 of the top section 112 is not visible but it is to be noted that the UV tubes 111 are present and the non-arrow line from 111 is intended to illustrate this).

FIG. 1D also illustrates a valuable item of media (currency or currency note) 150 being urged on the transport path of cassette 110 back towards the interface that ejects the note 150 from the dispense module 100 indicating that the note 150 is making a second and final pass through cassette 110 where it will be fully sanitized when ejected out of the dispense module interface along the transport path for subsequent stacking and ejection out a pocket outfeed module of the transaction terminal. The note 150 previously passed along the transport path for the length of the UV tubes 111 between the middle section 113 and the bottom section 114, the note 150 was turned along the transport path and passed between middle section 113 and top section 112 (where it is depicted in FIG. 1D). So, the note 150 is passed for the length of cassette 110 twice before exiting cassette 110 and being deposited back on the original transport path for exiting the dispense module 100.

Figure 1E:
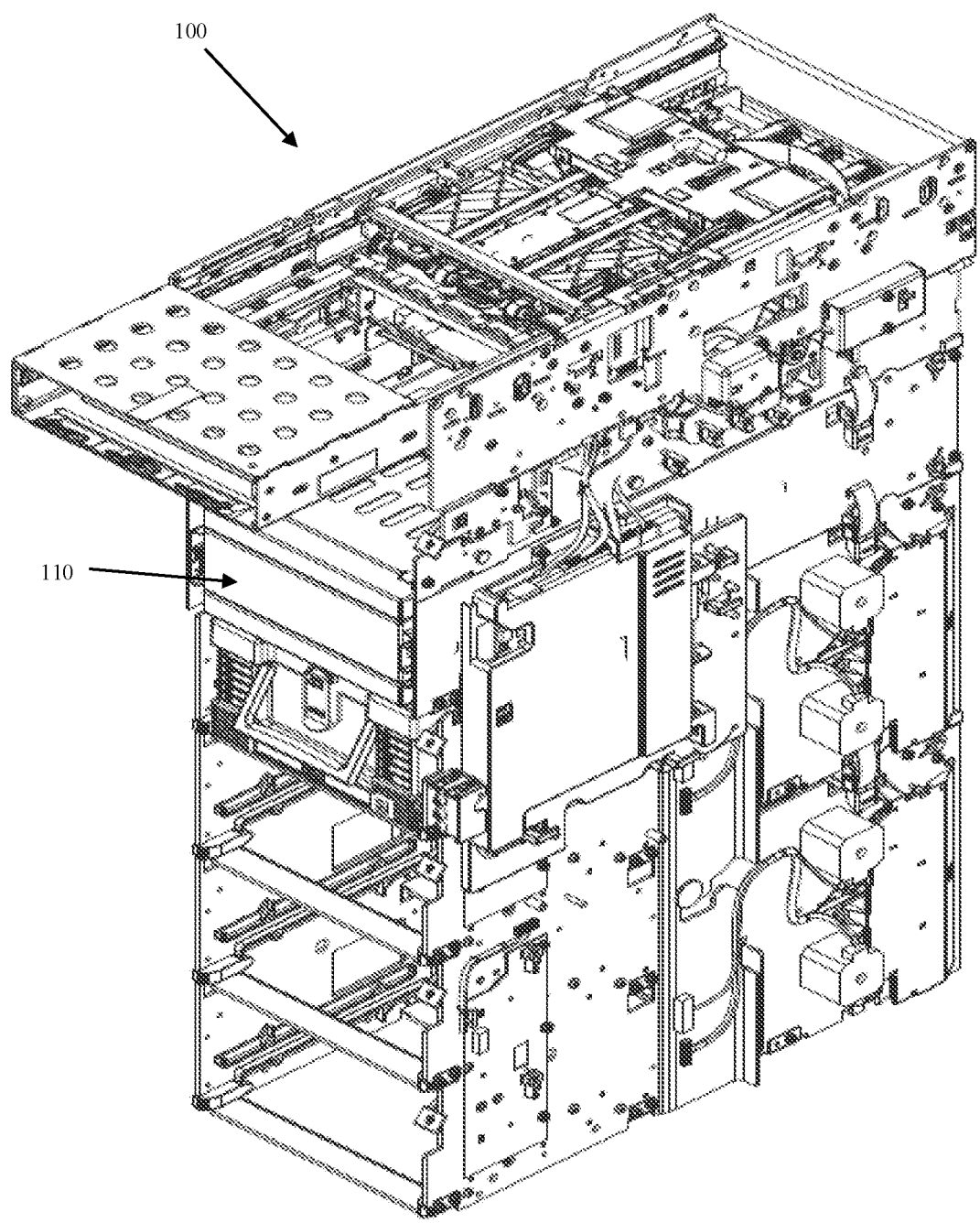
FIG. 1E is a diagram of a fully inserted and closed cleaning cassette, according to an example embodiment.

FIG. 1E is a diagram of a fully inserted and closed cleaning cassette 110, according to an example embodiment.

Figure 1F:
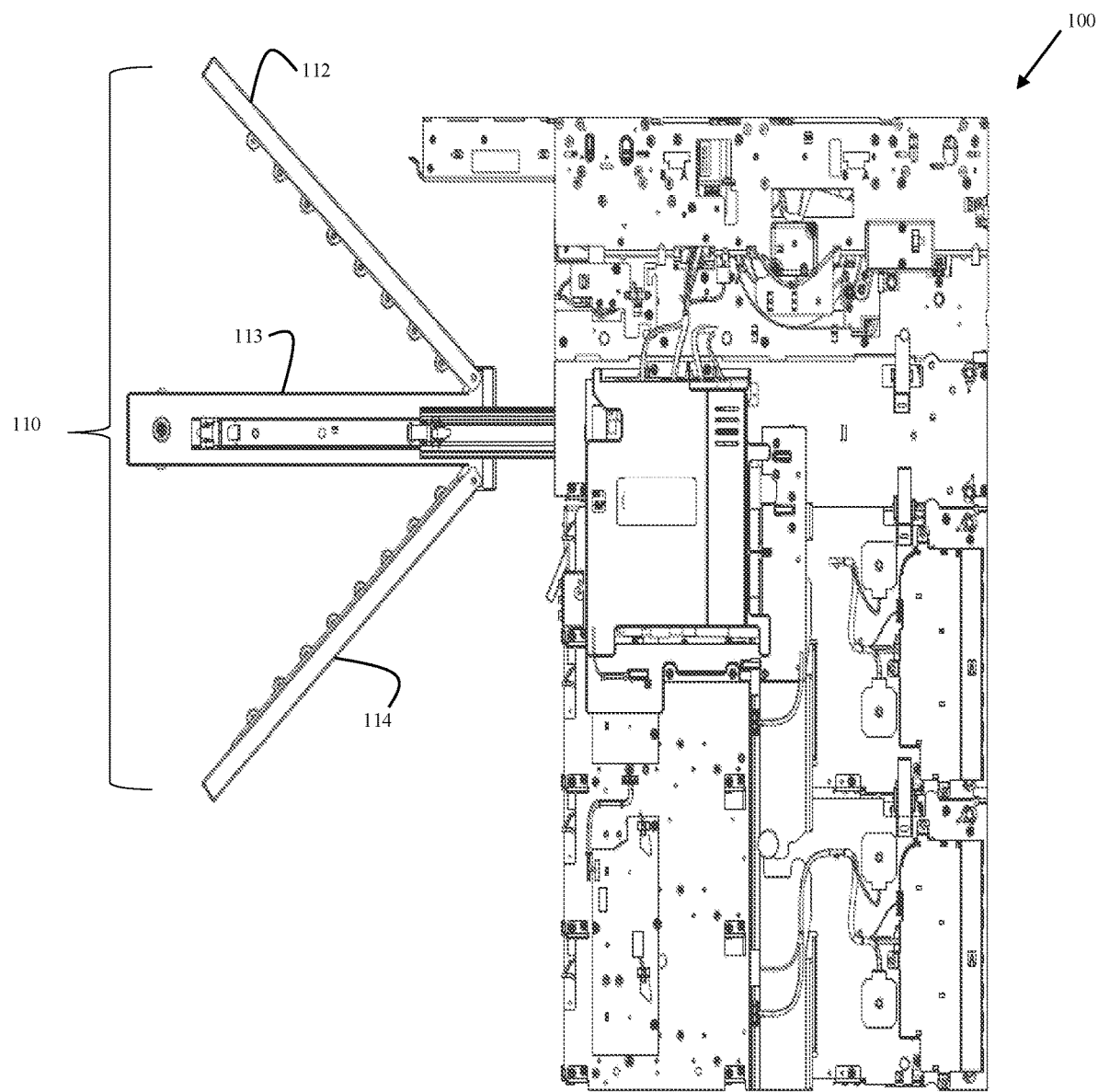
FIG. 1F is a diagram of a cross-sectional view of a partially removed and opened cleaning cassette, according to an example embodiment.

FIG. 1F is a diagram of a cross-sectional view of a partially removed and opened cleaning cassette 110, according to an example embodiment. Again, cassette 110 comprises a top section 112, a middle section 113, and a bottom section 114.

Figure 1G:
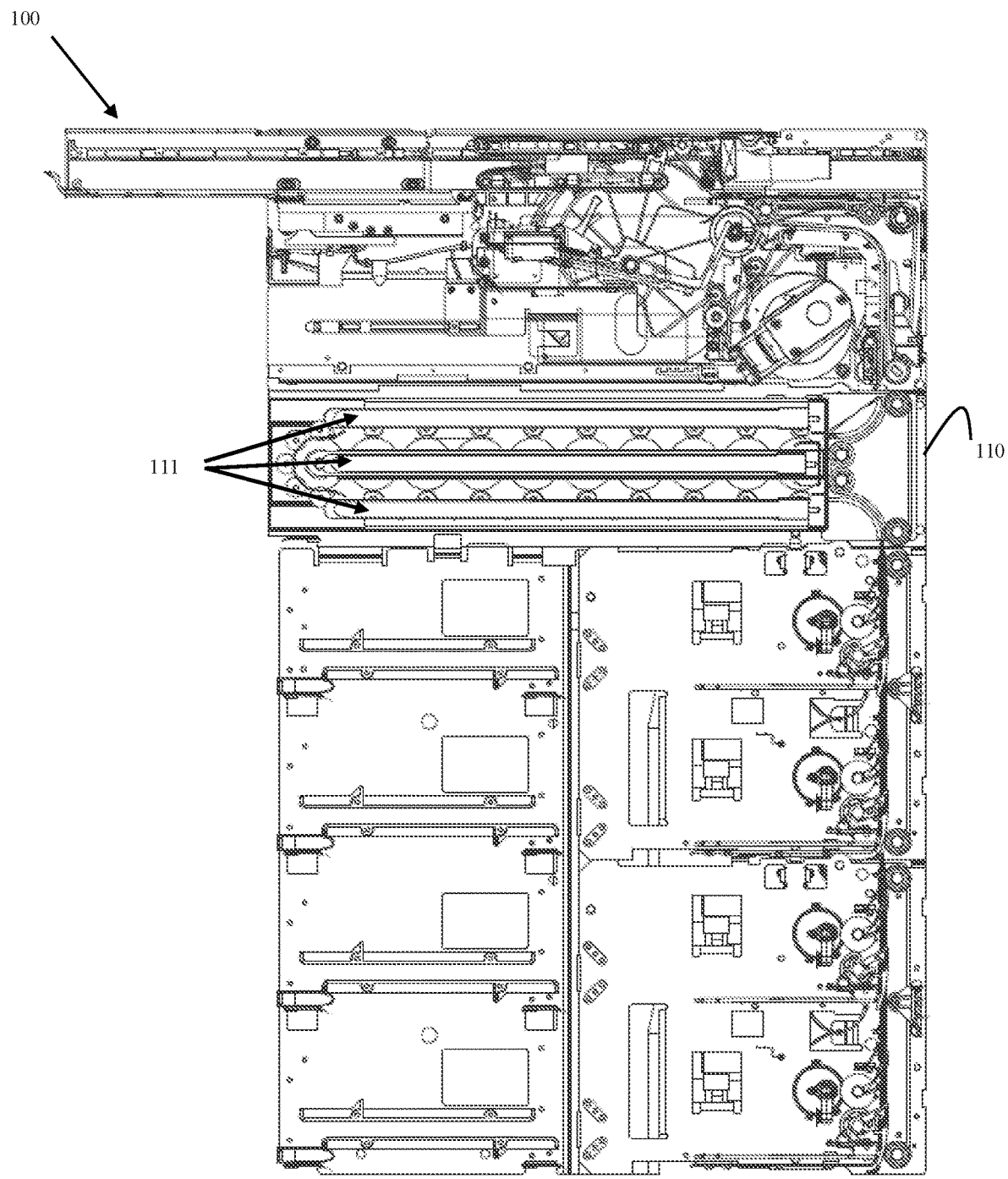
FIG. 1G is a diagram of a cross-sectional view of a fully inserted and closed cleaning cassette, according to an example embodiment.

FIG. 1G is a diagram of a cross-sectional view of a fully inserted and closed cleaning cassette 110, according to an example embodiment. Each second 112-114 includes 1 to 3 UV tubes 111 as shown in FIG. 1G.

Figure 1H:
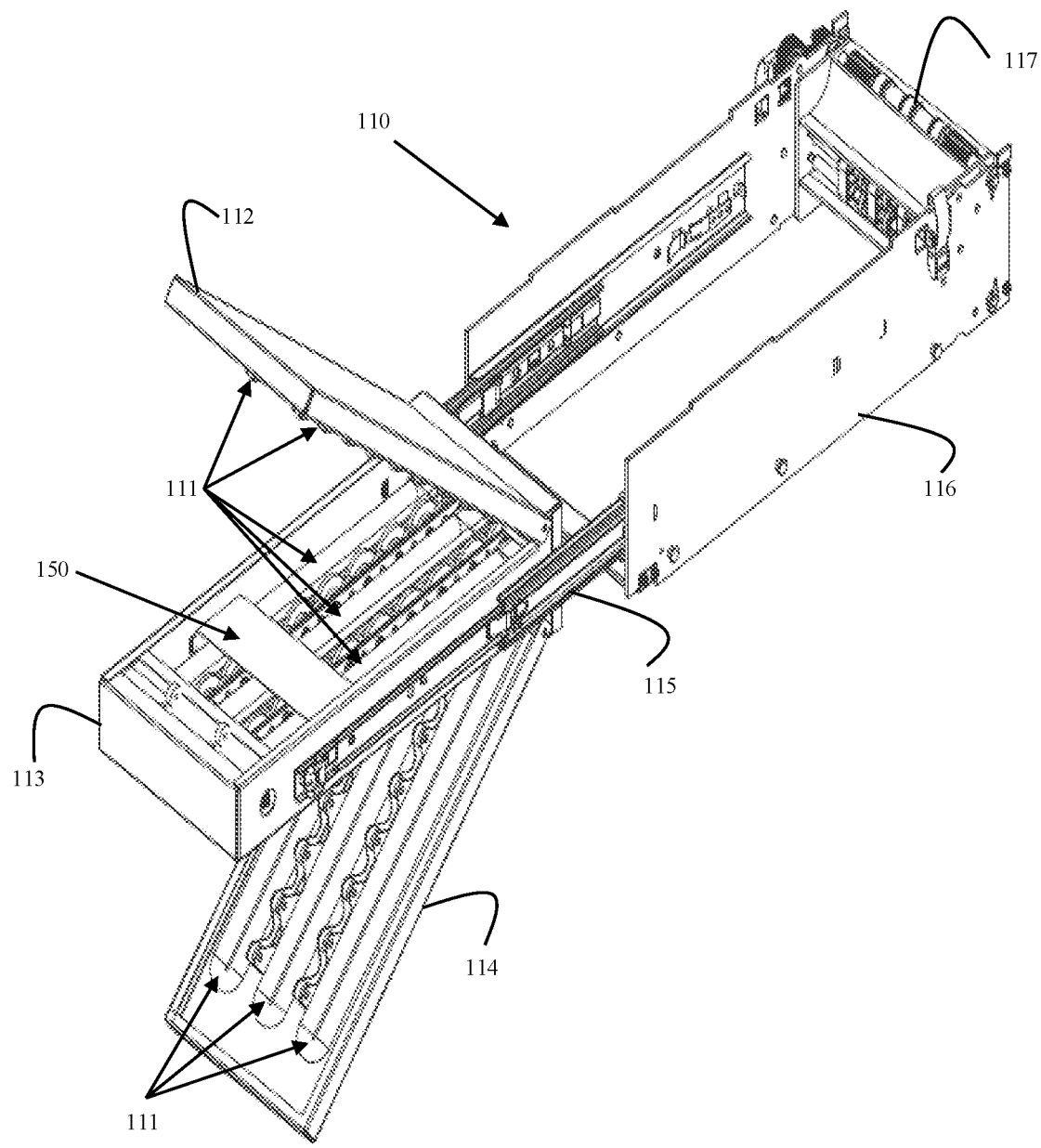
FIG. 1H is a diagram of a front view of a partially removed and opened cleaning cassette, according to an example embodiment.

FIG. 1H is a diagram of a front view of a partially removed and opened cleaning cassette 110, according to an example embodiment. The cassette 110 includes sides 116, rails 115, a top section 112, a middle section 113, a bottom section 114, and rear transport gears/interface 117. Each second 112-114 includes 1 to 3 UV tubes 111. Media item 150 is shown as being urged during the second pass through the cassette 110 between the top section 112 and the middle section 113.

Figure 1I:
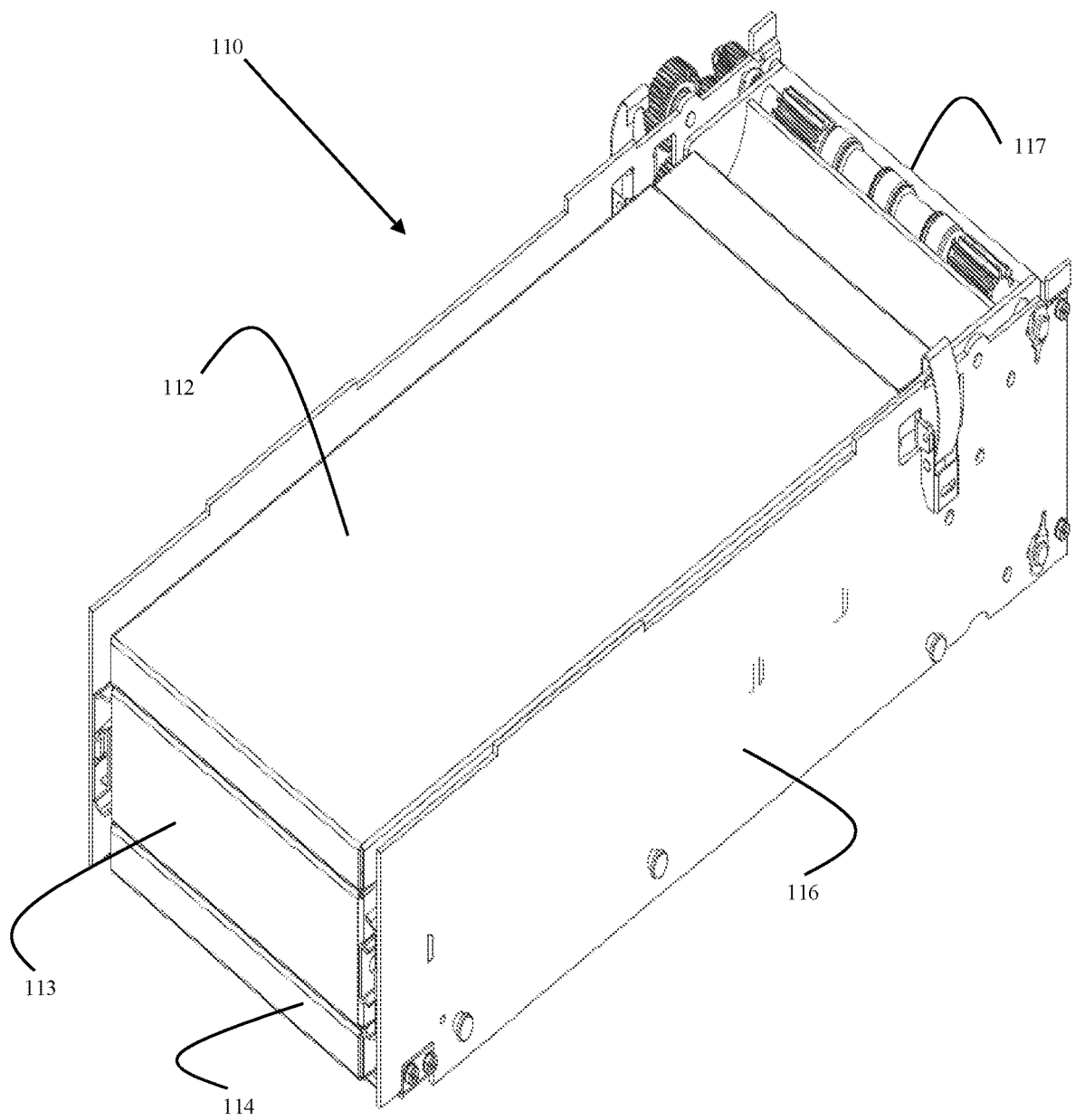
FIG. 1I is a diagram of a front view of a closed cleaning cassette, according to an example embodiment.

FIG. 1I is a diagram of a front view of a closed cleaning cassette 110, according to an example embodiment. In a closed orientation, cassette 110 is shown with top section 112, middle section 113, bottom section 114, sides 116, and rear transport gears/interface 117. The rear transport gears/interface 117 pick the media item off the transport path and onto a transport path within cassette 110 and the rear transport gears/interface place the media item back on the original transport path when the media item is fully sanitized and exits the cassette 110.

Figure 1J:
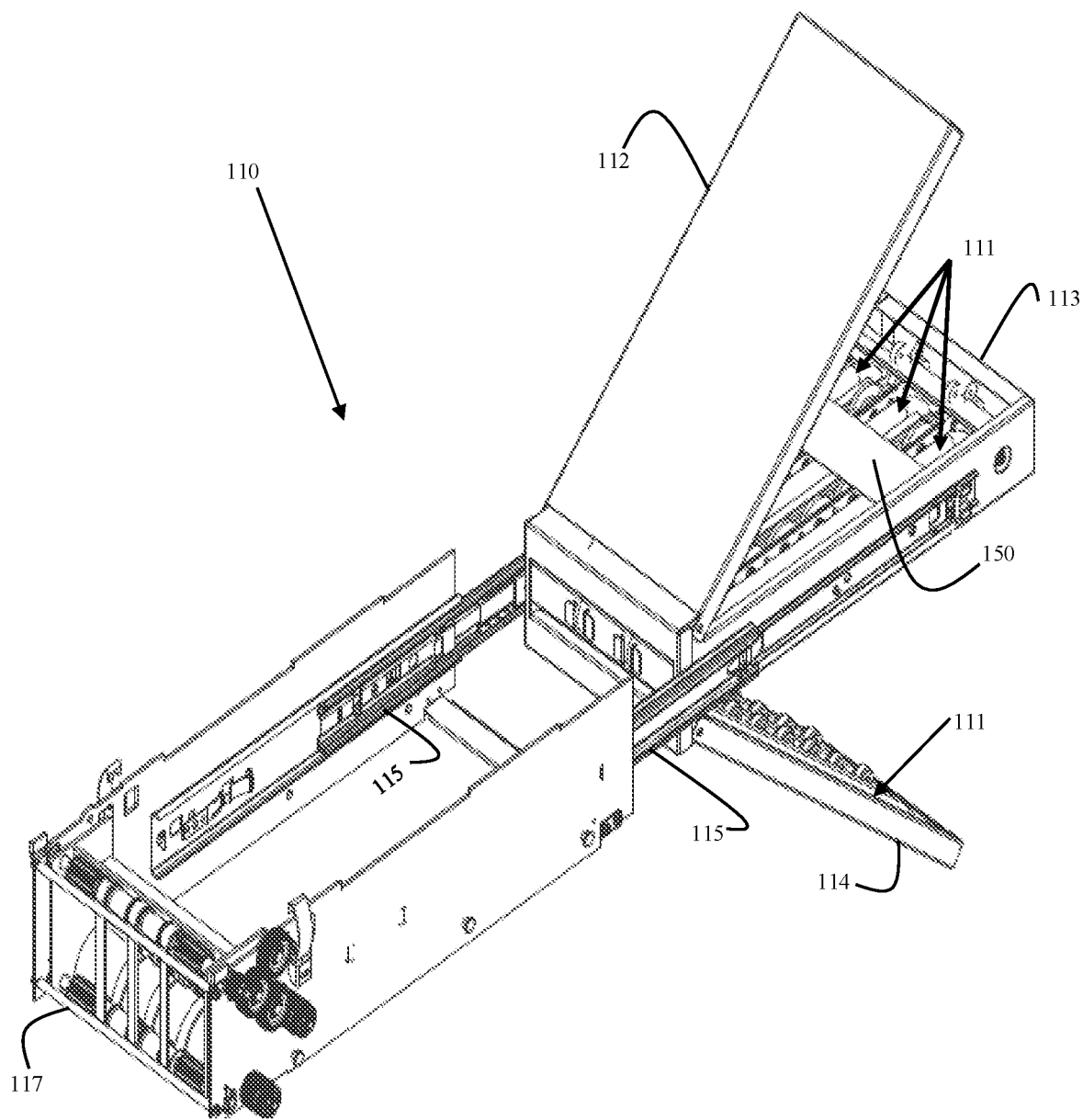
FIG. 1J is a diagram of a rear view of a partially removed and opened cleaning cassette, according to an example embodiment.

FIG. 1J is a diagram of a rear view of a partially removed and opened cleaning cassette 110, according to an example embodiment. Rails 115 can be seen in FIG. 1J and media item 150 passing between top section 112 and middle section 113 where both a top and a bottom of media item 150 is exposed to UV tubes 111.

Figure 1K:
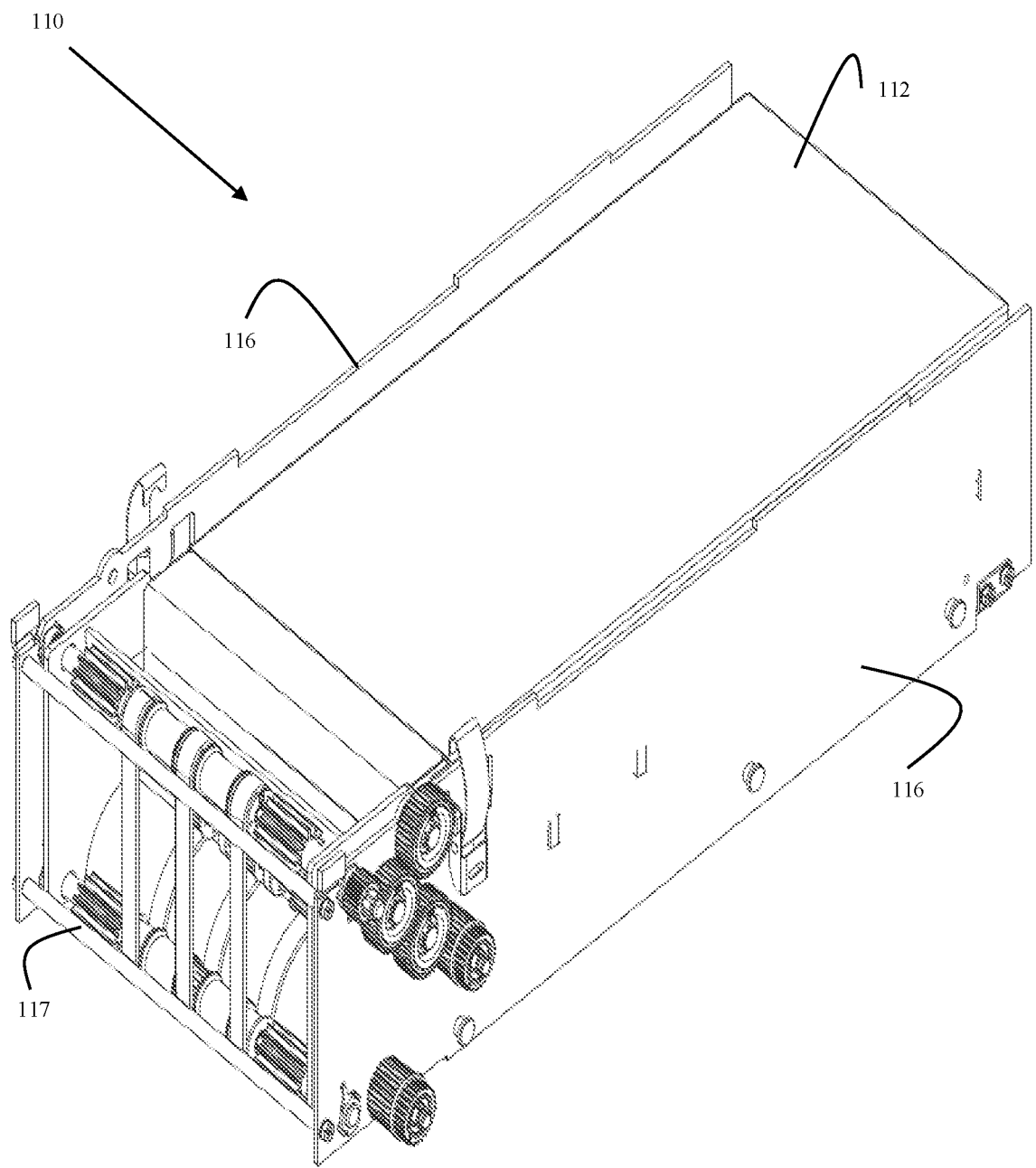
FIG. 1K is a diagram of a rear view of a closed cleaning cassette, according to an example embodiment.

FIG. 1K is a diagram of a rear view of a closed cleaning cassette, according to an example embodiment. FIG. 1K illustrates top section 112, sides 116, and rear transport gears/interface 117 of cassette 110.

Figure 1L:
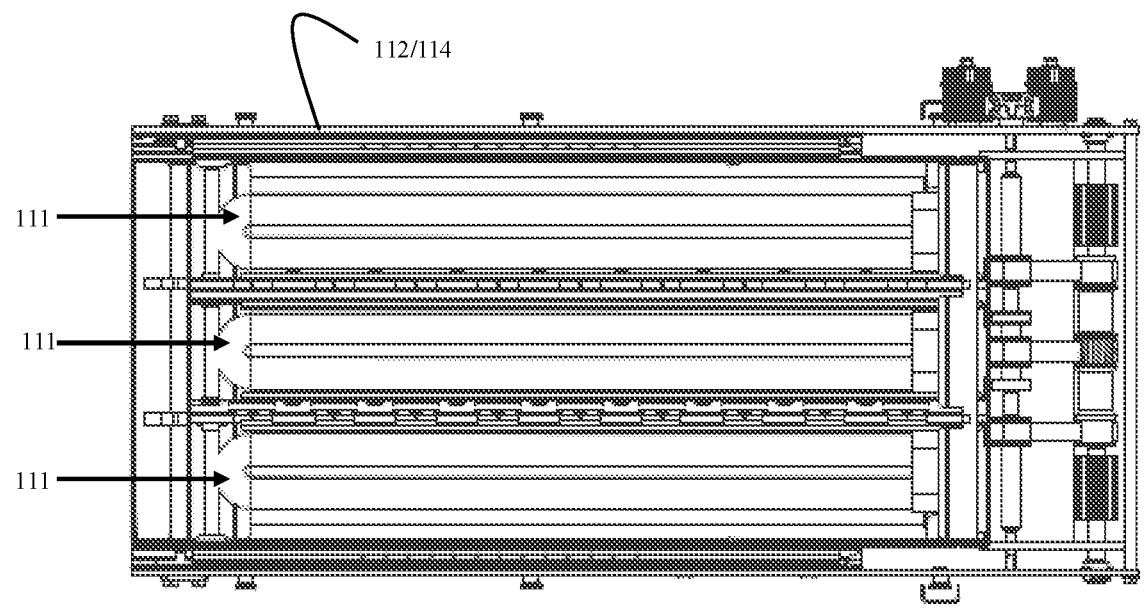
FIG. 1L is a diagram of a cross-sectional view of a top and/or bottom portion of a cleaning cassette, according to an example embodiment.

FIG. 1L is a diagram of a cross-sectional view of a top 112 and/or bottom portion 114 of a cleaning cassette 110, according to an example embodiment. Top 112 and/or bottom section 114 show three bending UV tubes 111. Each bending UV tube 111 passing the length of top 112 and/or bottom section/portion 114 for a length of cassette 110.

Figure 1M:
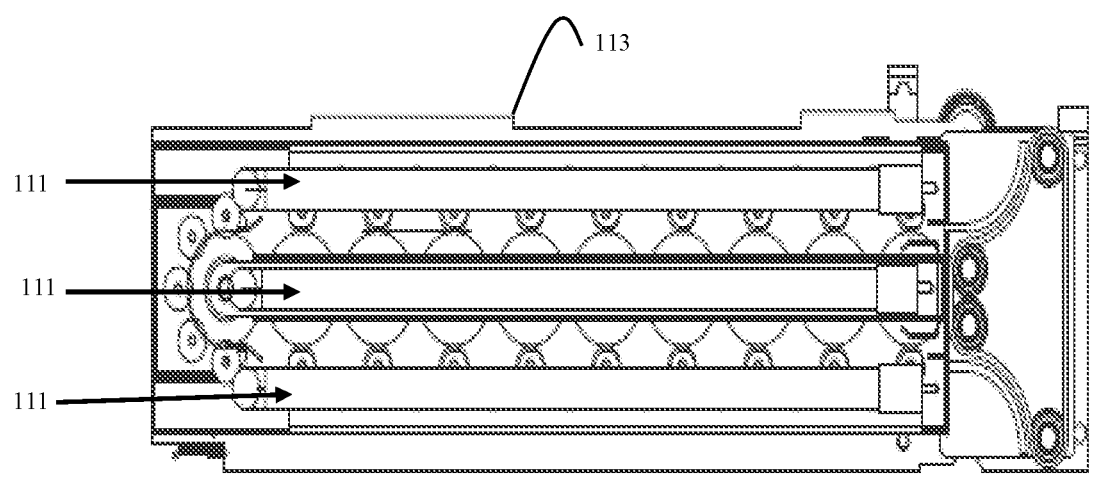
FIG. 1M is a diagram of a cross-sectional view of a middle/track portion of a cleaning cassette, according to an example embodiment.

FIG. 1M is a diagram of a cross-sectional view of a middle/track portion/section 113 of a cleaning cassette 110, according to an example embodiment. The middle section/portion 113 includes three UV tubes 111 that run the length of cassette 110. Unlike top 112 and bottom 114 section, the UV tubes 111 are each single non-bending UV tubes 111.

One now appreciates how a sanitizing/cleansing cassette 110 can be inserted into a dispenser module 100 or a recycler module 130 or 140 as a standard sized cassette 120 typically associated with media storage of a transaction terminal. The transport path within module 100, 130, and 140 is altered to urge media items being dispensed (or in some cases being deposited 140) through a two-pass length of cassette 110 where the top and bottom of the media item is exposed to UV radiation through UV tubes 111, which may kill or may eliminate up to 99% of bacteria and viruses, such as COVID-19, with a dose of UV radiation of approximately 40 mJ/cm². The cassette 110 comprises a fixed frame which replicates the geometry of a standard cassette pick module. The cassette 110 mounts into the dispenser 100 and/or recycler 130 or 140 using standard mounting features and retaining latches available in such dispenser modules 100 and recycler modules 130 or 140. The cassette 110 has a rear fixed rear belt transport which interfaces with the vertical transport of cassette pick modules. After notes passes through cassette the rear transport gear/interface 117 delivers the notes back to the original transport path and the standard interface. The rear transport interfaces with an enclosed metal box, which has an input and an output slot through which notes enters and leaves the main cleansing unit of cassette 110. The cassette 110 houses an array of mercury UV tubes 111, which fully irradiate both surfaces of each note 150 as the notes 150 transfer through the cassette 110. The transport system of cassette 110 is designed to maximize note UV exposure, thus given an even distribution of UV radiation across the entire surfaces (top and bottom) of the notes. The path that the notes travel within the cassette is maximized for twice the length of the cassette 110 (two passes) to create maximum UV exposure time. To ensure safe operation of the cassette 110, any user exposure is prevented through an entirely metal encased cassette 110 where users are completely shielded from passive UV light. The cassette 110 includes top 112 and bottom sections/covers that allow easy access to the transport path of the cassette should a note be jammed. The UV covers 112 and 114 cannot be removed while power to the deposit module 100 or recycler module 130 or 140 is on. That is, only when power is off can a latching mechanism allow covers 112 and 114 to be separated and opened. The power is cut when the cassette 110 is undocked from the deposit module 100 or recycler module 130 or 140. The cassette 110 is racked on built-in slides or rails allowing it to be pulled and undocked, which cuts power to the deposit module or recycler module 130 or 140, which then deactivates the latching mechanism and allows the top section 112 and the bottom section 114 to be opened. UVC (UV C light) mercury tubes are used as UV tubes 111 and are suspended within the cassette 110 with the notes being transferred along the length of the UVC mercury tubes twice. Roller and gear mechanisms are designed to allow the notes to pass as close to the UVC tubes 111 as possible to deliver virus and bacteria killing radiation onto the front and back surfaces of the notes.

In an embodiment, the media cleansing cassette 110 includes any bacteria and virus killing sanitizing lights or sanitizing system. The sanitizing system can include the UV tubes 111, any UV light capable of killing viruses or bacteria off of paper-based or polymer-based surfaces, etc.

In an embodiment, the UV tubes 111 are UVC mercury tubes.

In an embodiment, the UV tubes 111 are UVC LEDs or Far-UV LEDs with equivalent bacteria and virus sanitizing effects.

Use of UVC as a disinfectant source is an effective means of cleansing paper and polymer notes (media items 150) of the COVID-19 virus and other viruses.

In an embodiment, cassette 110 includes a tray arrangement or configuration instead of rails 115. In this way, any sliding mechanism may be used for removal of cassette 110 for the corresponding dispenser 100 or recycler 130 or 140.

These and other embodiments are now discussed with reference to FIGS. 2-4.

Figure 2:
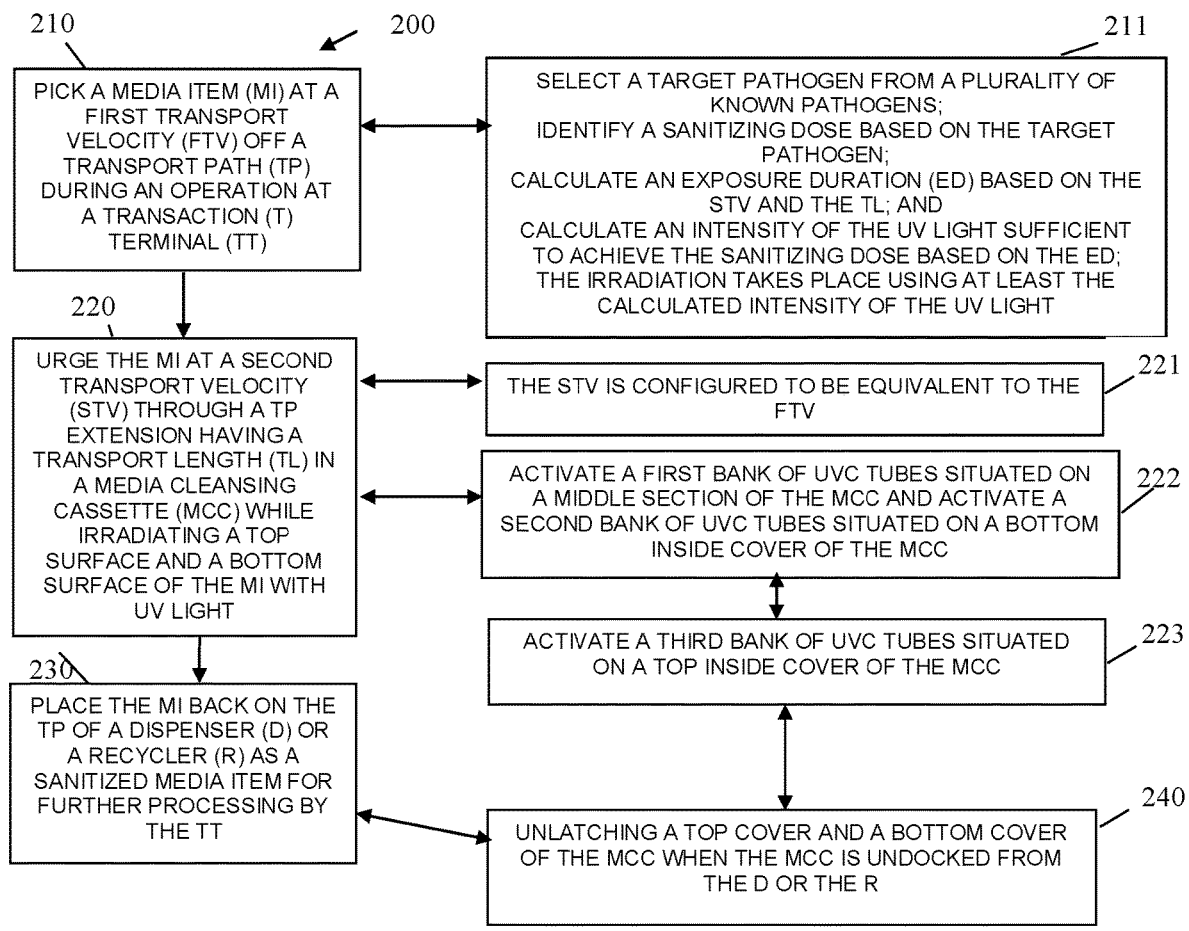
FIG. 2 is a diagram of a method of operating a cleaning cassette within a valuable media dispenser/recycler of a transaction terminal, according to an example embodiment.

FIG. 2 is a diagram of a method 200 of operating a cleaning cassette within a valuable media dispenser/recycler of a transaction terminal, according to an example embodiment. The software module(s) that implements the method 200 is referred to as a "media cleansing manager." The media cleansing manager is implemented as executable instructions programmed and residing within memory and/or a non-transitory computer-readable (processor-readable) storage medium and executed by one or more processors of a device. The processor(s) of the device that executes the media cleansing manager are specifically configured and programmed to process the media cleansing manager.

In an embodiment, the device is a motherboard associated with a novel media cleansing cassette 110.

In an embodiment, the device is a controller motherboard associated with a transaction terminal. The controller motherboard is connected through electronic circuitry to the electromechanical components of the novel media cleansing cassette 110.

At 210, the media cleansing manager picks a media item at a first transport velocity off a transport path during an operation at a transaction terminal within a dispenser 100 or a recycler 130 or 140.

In an embodiment, at 211, the media cleansing manager selects a target pathogen from a plurality of known pathogens, identifies a sanitizing dose of radiation based on the target pathogen, calculates an exposure duration based on a second transport velocity and a transport length of the media cleansing cassette, and calculates an intensity of the UV light sufficient to achieve the sanitizing does based on the exposure duration. The irradiation takes place using at least the calculated intensity of the UV light.

At 220, the media cleansing manager urges the media item at the second transport velocity through a transport extension having the transport length in the media cleansing cassette 110 while irradiating a top surface and a bottom surface of the media item with UV light.

In an embodiment, at 221, the media cleansing manager configures the second transport velocity to be equivalent to the first transport velocity.

In an embodiment, at 222, the media cleansing manager activates a first bank of UVC tubes situated on a middle section of the media cleansing cassette and activates a second bank of UVC tubes situated on a bottom inside cover of the media cleansing cassette.

In an embodiment of 222 and at 223, the media cleansing manager activates a third bank of UVC tubes situated on a top inside cover of the media cleansing cassette.

At 230, the media cleansing manager places the media item back on the transport path of a dispenser or a recycler as a sanitized media item for further processing by the transaction terminal.

In an embodiment of 221 and 230, at 231, the media cleansing manager activates a third bank of UVC tubes situated on a top inside cover of the media cleansing cassette.

In an embodiment of 230 and 223, at 250, the media cleansing manager unlatches a top cover and a bottom cover of the media cleansing cassette when the media cleansing cassette is undocked from the dispenser or the recycler.

Figure 3:
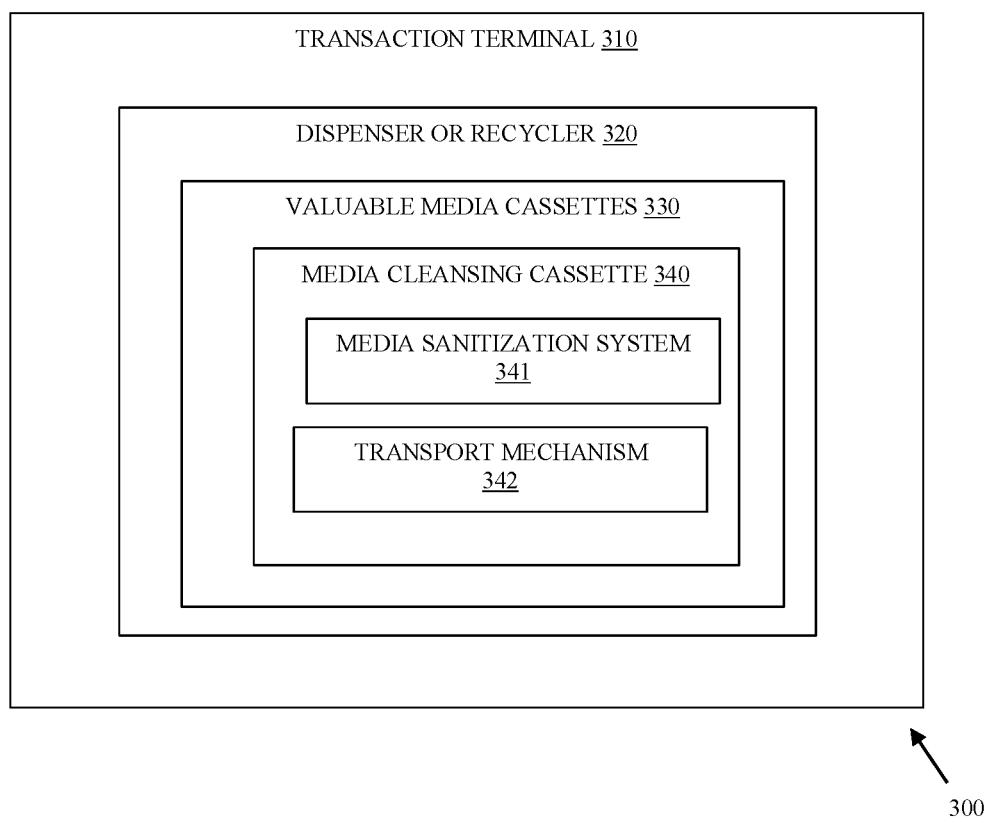
FIG. 3 is a diagram of a system for sanitizing media items, according to an example embodiment.

FIG. 3 is a diagram of a system 300 for sanitizing media items, according to an example embodiment. The system 300 implements, inter alia, the media sanitization or sterilization during deposit and/or dispense operations at a transaction terminal discussed herein and above.

The system 300 includes a transaction terminal 310, a dispenser 320 or a recycler 320, valuable media cassettes 330, and a media sterilization cassette 340.

In an embodiment, the system 300 includes dispenser 100 as dispenser 320.

In an embodiment, the system 300 includes a unidirectional note path recycler 130 as recycler 320.

In an embodiment, the system 300 includes a bidirectional note path recycler 140 as recycler 320.

In an embodiment, transaction terminal 310 is terminal 110. In an embodiment, terminal 110 is an ATM, a SST, or a POS terminal.

In an embodiment, valuable media cassettes 330 are valuable media cassettes 120.

In an embodiment, media sterilization cassette 340 is media cleansing cassette 110.

In an embodiment, system 300 treats or cleans valuable media that is deposited into one or more of the valuable media cassettes 330 during deposit transactions performed at the transaction terminal 110.

In an embodiment, system 300 treats or cleans valuable media that is being dispensed from the one or more valuable media cassettes 330 during dispense transactions at the transaction terminal 110.

In an embodiment, system 300 treats or cleans valuable media that is being deposited into one or more of the valuable media cassettes 330 during deposit transactions, and system 100 also treats or cleans valuable media that is dispensed from one or more of the valuable media cassettes 330 during dispense transactions.

Any deposited valuable media and/or dispensed valuable media is treated or cleansed by media cleansing cassette 340 during deposit transactions and/or dispense transactions at transaction terminal 310.

Media cleansing cassette 340 comprises a media sanitization system 341 and a transport mechanism 342.

In an embodiment, media sanitization system 341 is sanitizing system 111.

The sanitizing system 341 includes a radiation source and/or a heat source configured to treat, or cleanse valuable media items being transported through the media cleansing cassette 340 for purposes of mitigating and removing bacteria and viruses adhered on front and back surfaces of the valuable media items.

In an embodiment, sanitizing system 341 comprises one or more UVC mercury tubes, UV LEDs, Far-UV LEDS, Infrared (IR) heat source(s), antibacterial/antiviral sprays, or any combination of these items configured to deliver a dose of radiation, an amount of misted/sprayed antibacterial/antiviral liquid, and/or an amount of heat onto front and back surfaces of valuable media item as the valuable media is transported through the media cleansing cassette 330. The dose of radiation, the amount of liquid, and/or the amount of heat mitigates, treats, and/or removes any bacteria or viruses present on the front and back surfaces of the valuable media item.

The transport mechanism 342 includes an internal transport track and/or rollers that urge a valuable media item along a lower track and/or rollers for a length of media cleansing cassette 340, rotates the media item, and urge the valuable media item along an upper track and/or rollers for the length of the media cleansing cassette 340 where the cleansed or treated valuable media item is ejected out of the media cleansing cassette 340 where a transport path associated with the dispenser 320 of the recycler 320 obtains the cleansed valuable media item and transports the cleansed valuable media item into one of the valuable media cassettes 330 (for deposit transactions) or transports the cleansed valuable media item out of the dispenser 320 or the recycler 320 for delivery to a customer of transaction terminal 310 (for dispense transactions).

In an embodiment, the elapsed time taken by the dispenser 320 or recycler 320 for depositing media items and for dispensing media remains substantially unchanged from the perspective of a customer performing a deposit transaction or a dispense transaction at the transaction terminal 310 even though the media items traverse through the media cleansing cassette 340 for receiving bacteria and virus treatment provided by the media sanitization system 341.

The system 300 increases a length of the media path from conventional dispensers and recyclers by changing the conventional media path to cause media items to traverse through the media cleansing cassette 340 on two passes. A first pass of the media item through the cassette 340 is a lower pass between a bottom cover 114 and a middle section 113 of cassette 340. The media item is then rotated along the transport mechanism 342 and loops back for a second pass between a top cover 112 and the middle section 113. The media item includes a first surface and a second surface, during both passes a same surface that faced the middle section 113 remains facing the middle section 111 after the rotation or loop along the transport mechanism 342 whereas the opposite surface that during the first pass faced the bottom cover 114 is facing the top cover 112 during the second pass. The media item loops for two passes for a length of the transport mechanism 342. During each of the passes the front and back surfaces of the media item are treated or cleansed by the media sanitization system 341.

The amount of radiation, heat, and/or antibacterial/antiviral mist (liquid) delivered by media sanitization system 341 can be configured based on a length of the transport mechanism 342, a type of material that the media item is made of, a time taken for the media item to traverse the two passes, distances between the surfaces of the media item and the sanitization system 341, and a known type of bacteria/virus that is being removed or cleansed from the surfaces of the media item.

In an embodiment, a rate of travel for the media item to perform the two passes on the transport mechanism 342 can be sped up, slowed down, or otherwise adjusted based on the type of bacteria/virus that is being removed or cleansed from the surfaces of the media item. For example, a rate of performing the two passes can be slowed down from an original rate in order to expose the two surfaces of the media item to radiation for a greater period of time during the two passes for bacteria/viruses requiring a longer exposure rate to be neutralized or cleansed from surfaces of the media item.

In an embodiment, the dosage/amount of radiation, heat, and/or antibacterial/antiviral mist can be configured based on the type bacteria/virus being treated and the type of materials that comprise the media item to effectively mitigate the bacteria/virus from surfaces of the media item without any noticeable time delay being detected by a customer that is performing a deposit transaction and/or a dispense transaction at transaction terminal 310.

In an embodiment, a bidirectional note path recycler 320 sanitizes media items during deposit transactions by 1) routing each of the media items from an original transport path (track/rollers) through the media cleansing cassette 340 onto the internal transport mechanism 342 of the media cleansing cassette 340, 2) activating the media sanitization system 341 for treating both surfaces of the media item, urging the media item for a length of the transport mechanism 342 during a lower pass, 3) looping the media item along the transport mechanism 342 for an upper pass, 4) ejecting the media item out of the media cleansing cassette 340 back on the original transport path of the dispenser 320, and 5) depositing the media item into the appropriate valuable media cassettes 330.

In an embodiment a unidirectional dispenser 320 or a unidirectional recycler 320 sanitizes media items during dispense transactions by 1) routing each of the media items from an original transport path (track/rollers) through the media cleansing cassette 340 onto the internal transport mechanism 342 of the media cleansing cassette 340, 2) activating the media sanitization system 341 for treating both surfaces of the media item, urging the media item for a length of the transport mechanism 342 during a lower pass, 3) looping the media item along the transport mechanism 342 for an upper pass, 4) ejecting the media item out of the media cleansing cassette 340 back on the original transport path of the dispenser 320 or recycler 320, and 5) ejecting the media item out of a media interface associated with dispenser 320 or recycler 320.

Figure 4:
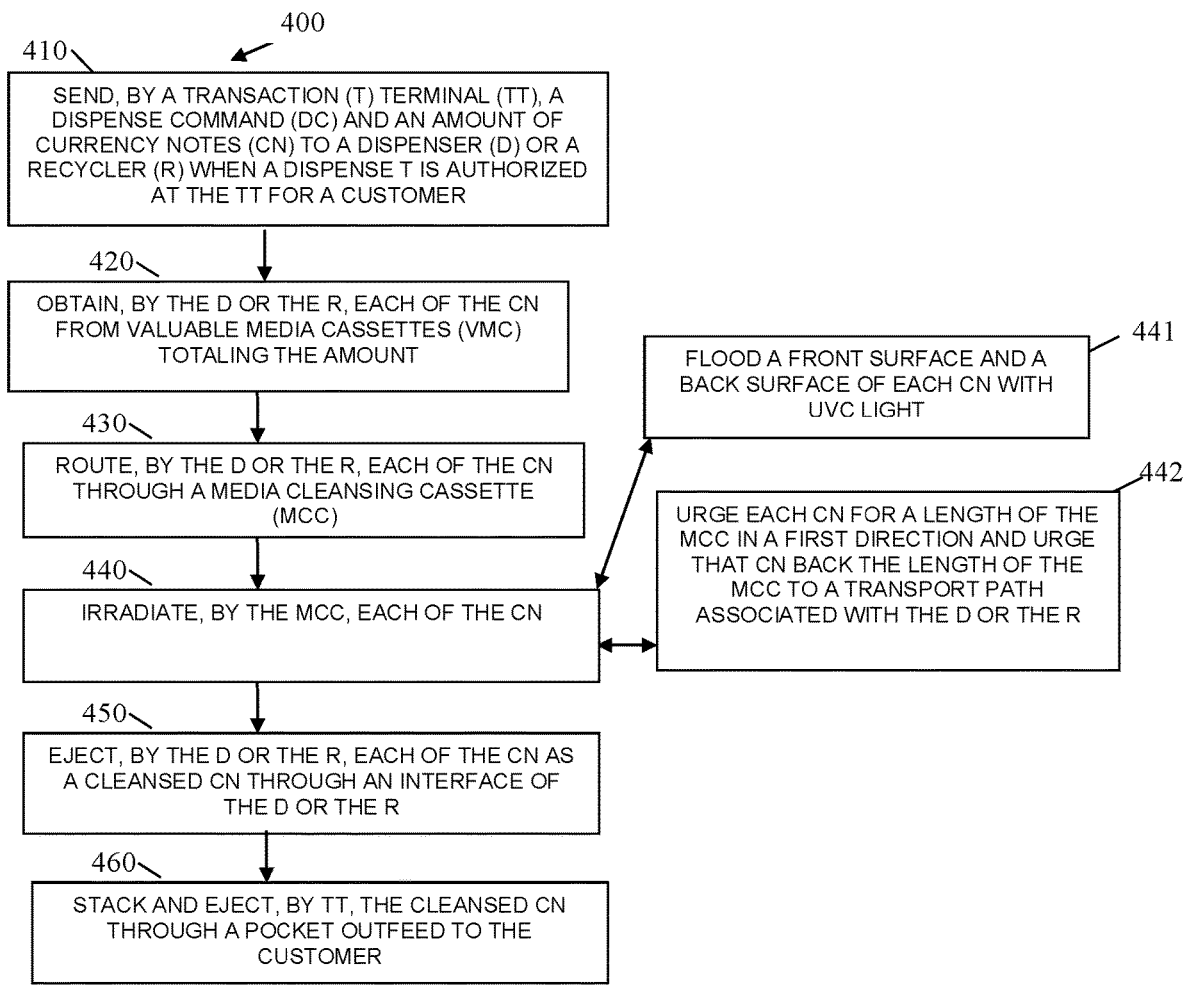
FIG. 4 is a diagram of another method for sanitizing media during a dispense transaction at a transaction terminal, according to an example embodiment.

FIG. 4 is a diagram of another method 400 for sanitizing media during a dispense transaction at a transaction terminal, according to an example embodiment. The software module(s) that implements the method 400 is referred to as a "currency note dispensing manager." The currency note dispensing manager is implemented as executable instructions programmed and residing within memory and/or a non-transitory computer-readable (processor-readable) storage medium and executed by one or more processors of one or more devices. The processors that execute the currency note dispensing manager are specifically configured and programmed to process the currency note dispensing manager.

In an embodiment, the currency note dispensing manager is processed by processors associated with a transaction terminal, dispenser 100 or recycler 130 or 140, and a media cleansing device 110.

In an embodiment, a motherboard associated with the transaction terminal includes electronic circuitry connecting to and controlling electromechanical components of the dispenser 100 or the recycler 130 or 140 and the media cleansing device 110.

In an embodiment, some portions of the currency note dispensing manager are processed on a processor of the transaction terminal and other components are processed on a different processor of the dispenser 100 or the recycler 130 or 140.

It is to be noted that the currency note dispensing manager, which is part of a bidirectional recycler may also include executable instructions that sanitize deposited media by processing the deposited media through the media cleansing cassette 110. So, the currency note dispensing manager can be processed for both deposit operations and dispense operations in cases where there is a bidirectional recycler.

Similarly, in some embodiments, a transaction terminal may include two media cleansing cassettes 110 one associated with the deposit media path and one associated with the dispense media path. In these embodiments, the currency note dispensing manager may be processed with both the deposit media path and the dispense media path.

At 410, the currency note dispensing manager (processing on the transaction terminal), sends a dispense command and an amount of currency notes to a dispenser 100 or a recycler 130 or 140 when a dispense transaction is authorized at the transaction terminal for a customer.

At 420, the currency note dispensing manager (processing on the dispenser 100 or the recycler 130 or 140), obtains each of the currency notes from one or more valuable media cassettes 120 totaling the amount.

At 430, the currency note dispensing manager (processing on the dispenser or the recycler 130 or 140) routes each of the currency notes through a media cleansing cassette 110.

At 440, the currency note dispensing manager (processing on the dispenser 100 or the recycler 130 or 140 or the media cleansing cassette 110) irradiates each of the currency notes and the currency notes are urged for a length of the media cleansing cassette 110 in a first direction and then back for the length in a second and opposite direction.

In an embodiment, at 441, the currency note dispensing manager floods a front surface and a back surface of each currency note with UVC light.

In an embodiment, at 442, the currency note dispensing manager urges each currency note for a length of the media cleansing cassette 110 in a first direction and then urges that currency note back the length of the media cleansing cassette 110 to a transport path associated with the dispenser 100 or the recycler 130 or 140.

At 450, the currency note dispensing manager (processing on the dispenser 100 or the recycler 130 or 140) ejects each of the currency notes as a cleansed or sanitized currency note through an interface of the dispenser 100 or the recyclers 130 or 140.

At 460, the currency note dispensing manager (processing on the transaction terminal) stacks and ejects the cleansed currency notes as a stack of cleansed or sanitized currency notes through a pocket outfeed to the customer to complete the dispense command. Again, it is to be noted that recyclers 130 or 140 may include any interface, such that embodiments presented herein should not be limited to just pocket outfeeds as the interface for delivering dispensed media to the customer.

It should be appreciated that where software is described in a particular form (such as a component or module) this is merely to aid understanding and is not intended to limit how software that implements those functions may be architected or structured. For example, modules are illustrated as separate modules, but may be implemented as homogenous code, as individual components, some, but not all of these modules may be combined, or the functions may be implemented in software structured in any other convenient manner.

Furthermore, although the software modules are illustrated as executing on one piece of hardware, the software may be distributed over multiple processors or in any other convenient manner.

The above description is illustrative, and not restrictive. Many other embodiments will be apparent to those of skill in the art upon reviewing the above description. The scope of embodiments should therefore be determined with reference to the appended claims, along with the full scope of equivalents to which such claims are entitled.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus, the following claims are hereby incorporated into the Description of the Embodiments, with each claim standing on its own as a separate exemplary embodiment.

The invention claimed is:

1. A method, comprising:
   urging a media item during a dispense operation around a sanitizing cassette that treats pathogens on the media item before the media item is dispensed, wherein urging further includes:
      urging the media item out of a media cassette onto a transport path around the sanitizing cassette and out of a media outfeed to complete the dispense operation.

2. The method of claim 1 further comprising, urging a second media item during a deposit operation around the sanitizing cassette that threats pathogens on the media item before the media item is deposited into a particular media cassette.

3. The method of claim 2 wherein urging further includes activating the sanitizing cassette when the second media item is deposited through a media infeed for depositing into the particular media cassette during the deposit operation.

4. The method of claim 1, wherein urging further includes activating the sanitizing cassette when the media item is dispensed from the media cassette for dispensing during the dispense operation.

5. The method of claim 1, wherein activating ultraviolet (UV) lights situated along a first portion and a second portion of the transport path associated with the sanitizing cassette when the media item passes around the sanitizing cassette before being ejected to complete the dispense operation.

6. The method of claim 5, wherein the UV lights comprise a first set of UV lights enclosed in a first tube along the first portion of the transport path adjacent to a first side of the sanitizing cassette, and wherein the UV lights comprise a second set of UV lights enclosed in a second tube along the second portion of the transport path adjacent to a second side of the sanitizing cassette.

7. The method of claim 6, wherein urging further includes urging a front surface of the media item facing the first side of the sanitizing cassette along the first portion of the transport path, causing the media item to turn and urge back along the second portion of the transport path with a back surface of the media item facing the second side of the sanitizing cassette while the first tube of the first set of UV lights and the second tube of the second set of UV lights are activated to treat the front surface and the second surface of the media item for pathogens.

8. The method of claim 7, wherein the transport path includes a third portion oriented vertically, wherein the first portion and the second portion of the transport path are oriented horizontally around the sanitizing cassette, and wherein the first portion and the second portion of the transport path are connected to the third portion of the transport path.

9. The method of claim 8, wherein the media item is urged vertically upward from the media cassette along the third portion of the transport path, urged horizontally on the first portion of the transport path, urged upward vertically along the transport path at an end of the sanitizing cassette, urged horizontally on the second portion of the transport path, urged vertically upward along the third portion of the transport path, and ejected through a media infeed or outfeed to complete the dispense operation.

10. The method of claim 1 further comprising, operating the method within a media depository of a terminal.

11. The method of claim 10, wherein the terminal is an automated teller machine, a self-service terminal, or a point-of-sale terminal.

12. A method, comprising:
   sanitizing a media item during transport within a media depository to treat the media item for pathogens before the media item is dispensed from a terminal associated with the media depository or before the media item is stored in a media cassette of the media depository, wherein sanitizing further includes:
      urging the media item in a loop along a transport path of the media depository during sanitization to sanitize a front surface and a back surface of the media item.

13. The method of claim 12, wherein sanitizing further includes activating ultraviolet lights along the loop to sanitize the front surface and the back surface of the media item.

14. The method of claim 12 further comprising processing the method within the media depository.

15. The method of claim 14, wherein the media depository is an integrated peripheral of the terminal.

16. The method of claim 15, wherein the terminal is an automated teller machine, a point-of-sale terminal, or a self-service terminal.

17. A terminal, comprising:
   a media depository comprising a processor, media cassettes, a media transport path, and a sanitizing media cassette; and
   the processor configured to:
      sanitize media items by urging deposited media items being deposited into the media cassettes;
      urge dispensed media items being ejected from the media cassettes along the media transport path around the sanitizing media cassette before the deposited media items are deposited and before the dispensed media items are ejected out of the terminal; and during urging along the transport path urge the media item in a loop along the transport path of the media depository during sanitization to sanitize a front surface and a back surface of the media item; and wherein the sanitizing media cassette configured to treat pathogens on front and back surfaces of the deposited media items and the dispensed media items.

18. The terminal of claim 17, wherein the terminal is an automated teller machine, a point-of-sale terminal, or a self-service terminal.

\* \* \* \* \*